(12) United States Patent
Kay

(10) Patent No.: US 7,347,112 B2
(45) Date of Patent: Mar. 25, 2008

(54) AIR SAMPLER WITH INTEGRATED AIRFLOW SENSING

(75) Inventor: Charles Gary Kay, San Antonio, TX (US)

(73) Assignee: Environemental Monitoring Systems, Inc., Charleston, SC (US)

( * ) Notice: Subject to any disclaimer, the term of this patent is extended or adjusted under 35 U.S.C. 154(b) by 221 days.

(21) Appl. No.: 10/711,585

(22) Filed: Sep. 27, 2004

(65) Prior Publication Data

US 2005/0241417 A1 Nov. 3, 2005

Related U.S. Application Data

(60) Provisional application No. 60/567,537, filed on May 3, 2004.

(51) Int. Cl.
*G01N 1/14* (2006.01)
*G01N 1/24* (2006.01)

(52) U.S. Cl. .................. 73/864.71; 73/863; 73/863.03; 73/864; 73/28.01; 73/28.05; 73/31.02; 73/31.03; 73/31.07

(58) Field of Classification Search .................. 73/863, 73/863.01, 863.03, 863.23, 864, 864.33, 73/864.34, 864.71, 864.73, 28.01, 28.05, 73/31.01, 31.02, 31.03, 31.07
See application file for complete search history.

(56) References Cited

U.S. PATENT DOCUMENTS

| 3,557,984 | A | * | 1/1971 | Rice | 228/160 |
|---|---|---|---|---|---|
| 3,603,155 | A | * | 9/1971 | Morris et al. | 73/863.01 |
| 3,965,748 | A | * | 6/1976 | Boubel et al. | 73/863.03 |
| 4,686,848 | A | * | 8/1987 | Casselberry et al. | 73/38 |
| 5,006,227 | A | * | 4/1991 | Behm et al. | 209/143 |
| 5,201,231 | A | | 4/1993 | Smith | |
| 5,479,812 | A | * | 1/1996 | Juntunen et al. | 73/1.34 |
| 6,692,553 | B2 | | 2/2004 | Jordan, Sr. et al. | |

FOREIGN PATENT DOCUMENTS

WO    WO 93/06910 A  *  4/1993   ................ 73/31.07

* cited by examiner

*Primary Examiner*—Daniel S. Larkin
(74) *Attorney, Agent, or Firm*—Moore & Van Allen, PLLC; Steven B. Phillips

(57) ABSTRACT

Air sampler with integrated airflow sensing. The air sampler according to at least some embodiments includes an air mover that is operable to move air over a sampling media. An integrated airflow sensor is in fluid communication with the air mover. The air mover operating speed can be adjusted, in example embodiments, by either a feedback control mechanism that is connected to the air mover and the integrated airflow sensor, by user input, or by a combination of the two. The feedback control mechanism adjusts the operating speed of the air mover in response to signaling from the integrated airflow sensor in order to maintain an actual airflow in accordance with a stored, target value. The feedback can, in at least some embodiments, compensate for obstructions, environmental variables, variations in the power supplied to the air mover, and the like.

41 Claims, 9 Drawing Sheets

| | |
|---|---|
| 0 | 0 LPM (special case) |
| 241 | 0-1 LPM |
| 221 | 1-2 LPM |
| 217 | 2-3 LPM |
| 216 | 3-4 LPM |
| 218 | 4-5 LPM |
| 219 | 5-6 LPM |
| 222 | 6-7 LPM |
| 227 | 7-8 LPM |
| 232 | 8-9 LPM |
| 237 | 9-10 LPM |
| 242 | 10-11 LPM |
| 244 | 11-12 LPM |
| 249 | 12-13 LPM |
| 253 | 13-14 LPM |
| 0 | 14-15 LPM |
| 5 | 15-16 LPM |
| 9 | 16-17 LPM |
| 11 | 17-18 LPM |
| 15 | 18-19 LPM |
| 16 | 19-20 LPM |

AIR SAMPLER WITH INTEGRATED AIRFLOW SENSING

CROSS-REFERENCE TO RELATED APPLICATION

This application claims priority from co-pending, provisional application Ser. No. 60/567,537, filed on May 3, 2004 by the inventor hereof, the entire disclosure of which is incorporated herein by reference.

BACKGROUND OF INVENTION

Most impacting air samplers work by directing a stream of the gas being sampled, usually air, onto a sampling media for a fixed period of time. The sampling media either is itself, or contains a flat piece of glass or plastic having a sticky surface adhesive which causes solids embedded in the air stream to stick as the air passes over it. This sampling media can then later be removed and microscopically analyzed. This sampling media may or may not contain an integrated orifice, which is used to concentrate incoming air onto a specific portion of the sampling media. An assembly for holding the sampling media in place may either be an integral part of the air sampler, or may be separate, in which case it is typically connected to the air sampler via air tubing. Note that in the later case, the term "air sampler" typically refers to the air mover, connections, controls, etc.

The accuracy and repeatability of this air sampling technique is dependent upon, among other things, the flow rate of sampled air directed onto the sampling media. The flow rate of air is usually measured in standard cubic feet or liters per minute with the word "standard" meaning equivalent to being measured at some specific temperature, barometric pressure, and humidity, for example, a temperature of 68 degrees Fahrenheit, 14.7 psi barometric pressure and 0% relative humidity. Adjustments of some kind are often needed to compensate for not being able to sample at the standard conditions.

Many current technology samplers use either a fixed or variable speed blower or pump to force the air onto the sampling media. A blower, pump, or any other apparatus to mechanically move air can be referred to as an "air mover" or "air moving arrangement." Those samplers with fixed speed air movers are adjusted at the factory or a calibration station for a specified airflow. Those with variable speed air movers often have a mechanical or electronic user adjustment option and may be supplied with a flow meter for aiding in this manual adjustment procedure. Samplers that have no air mover adjustment capability cannot be adjusted to compensate for changes in temperature, humidity and barometric pressure. For example, if a sampler was calibrated at 15 SLPM (standard liters per minute) airflow at sea level and is then shipped to a high-altitude location, the airflow will not be 15 SLPM for the same air mover speed, at least because there are fewer molecules in the air. Samples taken with such a sampler must be mathematically manipulated to compensate for such variables. In some cases, samples are inaccurate and/or cannot be used at all if the airflow is too low because particles do not impact the media properly. Samplers with adjustable speed air movers used in conjunction with mechanical flow meters can be adjusted for these variables, but the adjustments often have to be made manually every time a sampler is moved or conditions change, and there is no convenient way to re-adjust the sampler if conditions change during sampling. Also, the flow meter may restrict the airflow, possibly complicating the adjustment in that the meter's airflow restriction must be taken into account. The amount of restriction caused by the flow meter is dependent upon its technology.

The airflow in any sampler can also vary due to mechanical changes such as obstructions being introduced, placement and orientation of the media and orifice, build-up of sample material on the media, or air mover component wear and lubrication. Obstructions in the system can include, for example, collapsed or partially collapsed hoses and dirt in the air path or in exhaust and/or intake filters. Thus, adjustment or re-calibration is required at regular intervals to ensure accuracy in the face of such changes. Adjustments must also be made for various sampling setups, such as those that use extra air tubing to connect a more remote sampling media, or to draw air from inside a wall or other structure. Finally, bearing temperature and supply voltage for the air mover may change during sampling, adversely affecting accuracy even when a careful, skilled operator has calibrated the sampler taking all of the other factors into account.

SUMMARY OF INVENTION

An air sampler according to at least some embodiments of the present invention includes an air moving arrangement that is operable to draw air over a sampling media. An integrated airflow sensor is interfaced to the air moving arrangement so that fluid communication is provided between the air moving arrangement and the integrated airflow sensor. In some embodiments, a control system that is interconnected with the airflow sensor can use signaling produced by the sensor to provide a standard airflow indication as opposed to a volumetric airflow measurement to alleviate the need for an operator or user to perform calculations to determine standard airflow. Such a control system can also provide a way to store a history of environment and sample related readings for future reference.

In some embodiments, the air moving arrangement operating speed can be adjusted by the control system. The adjustment can be made in response to user input via an input device, or by a feedback control mechanism, or by a combination of the two either alone or in combination with still other means. The feedback control mechanism can be connected to the air moving arrangement and the integrated airflow sensor. The feedback control mechanism adjusts the actual or effective operating speed of the air moving arrangement in response to signaling from the integrated airflow sensor in order to substantially maintain a target airflow. The value of the target airflow to be maintained is stored within the air sampler, typically in a memory, which may be integrated with a controller. The feedback control mechanism will determine a current, measured airflow and adjust the air moving arrangement's speed accordingly to compensate for obstructions, environmental variables, and the like as necessary to substantially maintain the target airflow.

In some embodiments, one or more output signals from the airflow sensor is indicative of airflow. In other embodiments, two output voltages, which are indicative of temperatures, are sensed and a temperature difference is indicative of airflow. In other embodiments, an airflow sensor that includes a mechanical linkage can be used. In still other embodiments, the signaling from the airflow sensor can be a digital data stream. The signaling from the airflow sensor can be used to determine standard airflow, which can in some embodiments then be used to make adjustments to the sampler's operating parameters, such as the effective air mover speed.

In some embodiments, a user display device is provided to display, possibly among other things, current airflow. Additionally or alternatively, a user input device can be provided to allow a user to change the desired, actual airflow or set the target airflow for a feedback control mechanism, which alters the stored, target value, at which point the feedback automatically adjusts actual airflow to match the target value as closely as possible. External environmental sensors can be provided, such as for temperature, humidity, and barometric pressure. Readings from these sensors can be used in determining the standard airflow that is being indicated by the integrated airflow sensor, or can be recorded for future reference. In the case of a self-contained unit, an integrated sampling media assembly may be included.

In embodiments with a controller based feedback control mechanism, hardware alone, or hardware combined with microcode, software or firmware stored in memory, either inside or external to the controller causes the controller to carry out methods necessary to implement embodiments of the invention. These methods may include starting and stopping the air mover, calculating and measuring airflow based on signaling from the integrated airflow sensor, a null offset value for the integrated airflow sensor, a linearity characteristic for the integrated airflow sensor, previously stored calibration data, current environmental readings or a combination of the above. These methods may also include comparing the measured airflow to a stored, target value, and adjusting the operating speed of the air mover based on the result of the comparison. The sampling process may be repeated for a plurality of sampling periods. Various time thresholds or waiting periods may be established for adjusting the air mover speed based on the result of the comparison between measured and stored, target airflow values. Thus, the air mover operating speed might be adjusted less often or not at all if the measured airflow is close to its stored, target value. In example controller-based embodiments, the controller, sensors, connections, and software instructions form the means to carry out the various processes of the invention.

DETAILED DESCRIPTION

Figure 1:
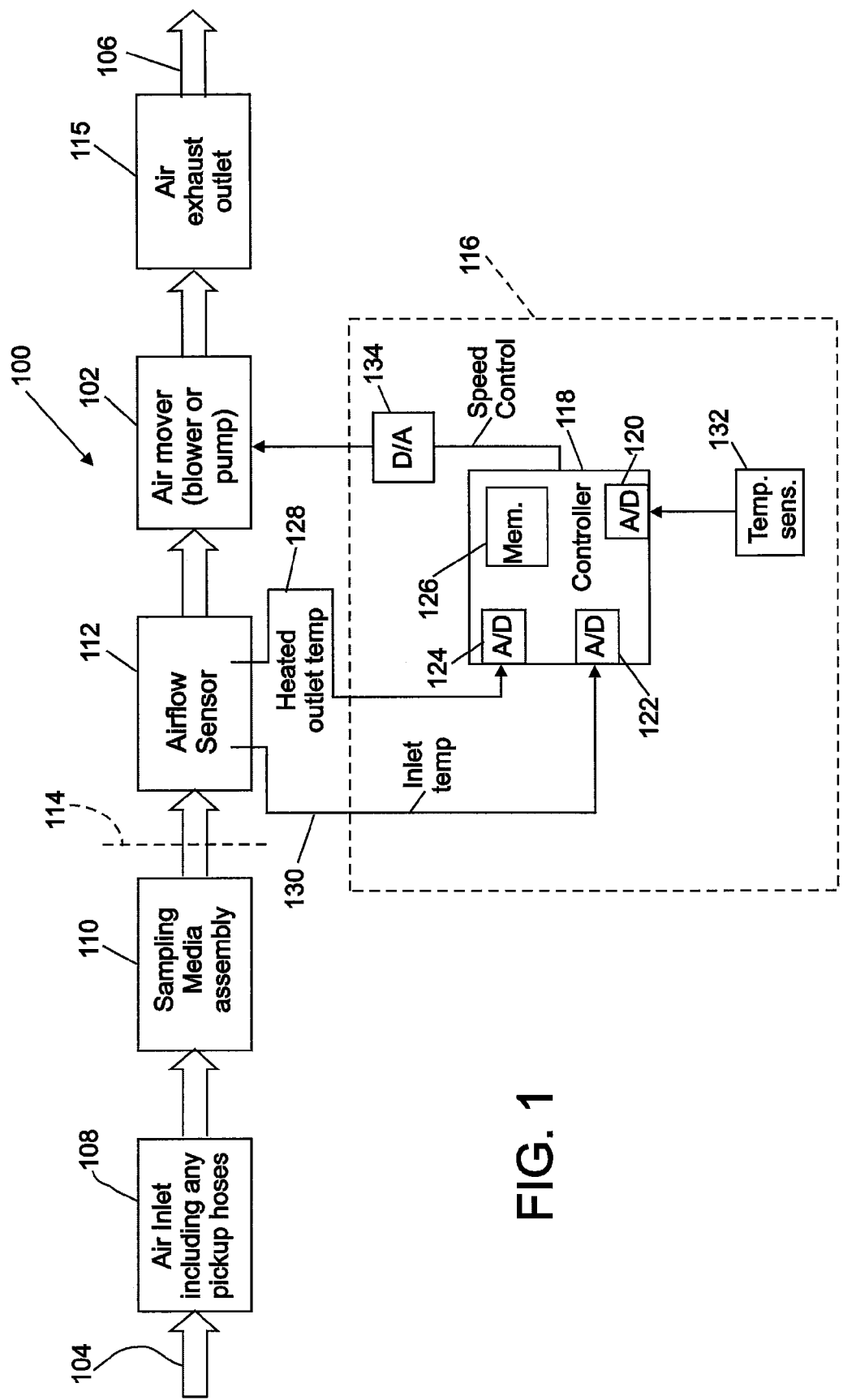
FIG. 1 is a functional block diagram including an air sampler according to one embodiment of the invention.

The present invention will now be described more fully with reference to the accompanying drawings, in which specific embodiments of the invention are shown. The invention may, however, be embodied in many different forms and should not be construed to be limited to the specific embodiments herein. In some of the drawings, various structures may not be shown where the clarity of other aspects of the drawing is important to understanding an embodiment. Also, like reference numbers refer to like elements throughout the description of the drawings.

It may be helpful to the reader if some of the terminology used in this description is understood from the beginning. Other terms are defined when first used or should be assumed to have their customary meaning in the art. As previously mentioned, the terms "air mover" or "air moving arrangement" can refer to a pump, fan, or any other type of mechanical, electrical, or electro-mechanical device that pushes, pulls, or draws air. The term "integrated airflow sensor" refers to any integrated device, which produces electrical or mechanical indications that can be used to determine actual airflow, either directly or indirectly. The use of the term "integrated" in this context means that the sensor is designed to remain in the airflow and operate during normal use. In most cases, such a sensor is physically integral to a finished air sampler device, but a sampler that uses a physically separate sensor that is plugged in or connected as part of the device set-up can nevertheless be considered to have an "integrated airflow sensor" for purposes of this disclosure. Note also that the airflow sensor can be combined with other components. For example, an airflow sensor can be combined in a single, off-the-shelf unit with the control system, in which case a connection between these two may be internal to the unit. Such a device may still have external connections for power, and for the air moving arrangement, and an air sampler using such a device does not depart from the spirit or scope of the invention.

For the airflow sensor as well as other mechanical and also electrical components, when elements are referred to as being "connected," "interfaced," or in "communication" this connection can be either electrical or mechanical, and either direct or indirect; that is with other components intervening. The term "air" can refer to any gas that can be moved by an air mover. Although it will typically be indoor or outdoor breathing air, it does not necessarily have to be. It could also be other gases, and may have contaminants.

Airflows herein are referred to as "actual airflow," "measured airflow," and "stored airflow" or a "stored and/or target value" for airflow. Actual airflow is usually referring to physical airflow through a sampling device. It can be expressed in any units, and may be either mass-based or volume-based. The "measured airflow" is the actual airflow as determined by the air sampler. If a sampler is functioning properly, "measured airflow" can be assumed to be substantially the same as "actual airflow." Contrast this with a "stored value" or "stored target value" which is a numerical representation of an intended airflow stored in an electronic, mechanical, optical, or electromechanical memory device. Finally, notice that temperatures herein are discussed both with respect to temperatures measured inside an airflow sensor or the air sampler, and temperatures of the outside air being sampled. The latter is usually referred to as "external temperature" and can be measured by an "external temperature sensor" although there is recognition that such readings may be slightly affected by operating heat generated by the air sampler. Thus, the term "external temperature sensor"

can be integral to an air sampler device. The term "external" in this case simply means that the temperature being monitored is the temperature of the outside air.

As noted previously, airflow can be expressed as either the mass or volume of gas per time. It is common within the industry to express airflow as "standardized volumetric airflow in SLPM (standard liters per minute) or SCFM (standard cubic feet per minute). These are volumetric values "standardized" to specific air temperature and barometric pressure and are useful because they reflect the heat carrying capacity of the air. Regardless of how airflow is expressed, it must first be measured and there are several ways of measuring airflow. Some methods measure the velocity or deflection of an impeller, pith-ball, or other mechanical indicator and then readings must be arithmetically compensated temperature, barometric pressure and humidity to determine standard airflow in units, such as SCFM or SLPM. Some methods measure "mass airflow" and measurements do not need to be compensated. A sensor that uses the latter measurement method can be referred to as a mass airflow sensor. Sensors that measure using either technique are acceptable for implementing embodiments of the present invention.

The term "null offset" refers to the DC voltage output by an airflow sensor at zero airflow. The term "null shift-with-temperature" refers to the shift or change in this "null offset" voltage with temperature. The term "output shift-with-temperature" refers to the shift or change in the output voltage of the airflow sensor at non-zero airflow less the "null offset" voltage, as a function of temperature. As an example, in the case of the Honeywell AWM720P1 sensor discussed herein, it is expressed as a percentage of the reading.

As previously mentioned, an air sampler according to some embodiments of the present invention can overcome at least some of the need for repeated, tedious calibration and adjustment by including an integrated airflow sensor, that is, a sensor located in the air stream of the sampler. The airflow sensor can be interconnected with a feedback-based control mechanism, which automatically adjusts the blower, pump, or other air mover actual or effective operating speed as needed to maintain constant airflow. Even if the airflow sensor itself introduces a restriction into the system, it does not matter because the feedback control system has the ability to automatically increase the air mover speed as necessary to compensate for the added restriction. In the same way, the system compensates for all flow restrictions including pickup hoses, the orifice and/or sampling media and filters so long as the maximum capacity of the air mover is not exceeded. An air sampler according to such embodiments of the invention can be described as having "airflow feedback."

Either with or without a feedback control mechanism, a control system of an air sampler according to some embodiments of the invention can include a user input device and make use of an integrated airflow sensor to permit relatively accurate manual adjustment of airflow. The user input device may include an actuator or actuators that directly manipulate airflow, or buttons, or adjustable controls, either electrical or mechanical, that interface with a control or processor so that it can make appropriate adjustments. In some embodiments, the control system may additionally, or only, determine and provide standardized airflow from the integrated airflow sensor signaling.

There are several methods of measuring airflow. An airflow sensor can be constructed by placing two temperature sensors in an air tube. Each temperature sensor has an electrical interface and the tube, and therefore the temperature sensors, is/are placed in the air stream of the sampler during operation. One of the two temperature sensors is heated either internally or with a nearby heat source; while the other is not. The sensors can be located such that they are both subjected to substantially equal airflow, but not so close that the heater affects the unheated sensor. An example configuration would be to locate the unheated sensor nearer the tube inlet and the heated sensor nearer the tube outlet. When operated, the temperature of the heated sensor will almost always be warmer than the unheated sensor. This temperature difference is inversely proportional to airflow; the lower the airflow, the higher the temperature difference; and the higher the airflow, the lower the temperature difference. A control system in an embodiment of the invention using an airflow sensor like that just described can include a controller with analog-to-digital (A/D) conversion and memory. A feedback control mechanism in such an embodiment can include the controller repeatedly reading both temperatures and adjusting the air mover speed as necessary to maintain a preset temperature difference as indicating a measured airflow value substantially in accordance with a target value.

FIG. 1 is a block diagram of an embodiment of an air sampler that works on the principles just described. Air sampler 100 includes air moving arrangement 102, which can be a fan, pump, or other device. Air moving arrangement 102 is disposed to draw air through the system, following the path of the arrows. Air to be sampled enters at 104 and exhausts at 106. Air to be sampled enters the sampler's air inlet 108, which for illustrative purposes can be assumed in this example to include any pickup hoses or passages. Air then enters the sampling media assembly 110, which includes any slide or similar conveyance containing the media that is to capture the contaminants. Airflow sensor 112, which in this example works as described above, is disposed to be in fluid communication with, and in the path of the airflow between, sampling media assembly 110 and air moving arrangement 102. A filter 114, may optionally be included to protect airflow sensor 112, air moving arrangement 102, and other downstream components from larger contaminants and particulates. Air exits air exhaust assembly 115, which may include additional muffling to quiet the unit or filtering to protect the environment from small amounts of lubrication or dirt that may be added to the post-sampled air stream by the sampler. Any filtering lessens the likelihood that the sampler will inadvertently contaminate a previously uncontaminated environment. Control system 116 provides air mover control and can also provide airflow feedback as described above and will be discussed in greater detail below.

As previously discussed, the principles of the invention can be applied to a variety of types and configurations of air samplers. Thus, a sampling media assembly and sampler air inlet and/or pickup may be included in a self-contained unit. U.S. Pat. No. 5,201,231 describes such an air sampler, although without any airflow feedback, and is incorporated herein by reference. Air samplers in which the air mover is a pump typically do not, although may, have an integrated sampling media assembly. A separate sampling media assembly that can be used with such an air sampler and its use are both described in U.S. Pat. No. 6,692,553, which is incorporated herein by reference.

Returning to FIG. 1, control system 116 in this example includes controller 118. Controller 118 has built-in multi-channel A/D converter functionality, represented by A/D conversion blocks 120, 122, and 124. Controller 118 also has built-in memory, 126. An example of but one of many suitable controllers for implementing a feedback control system according to this example embodiment is the Microchip™ PIC18F452 microcontroller available from Microchip Technology, Inc. of Chandler, Ariz. USA. Signaling received from the airflow sensor by the microcontroller in this example includes signal voltage 128 representing the heated airflow sensor outlet temperature, which is fed to A/D conversion block 124, and signal voltage 130 representing the airflow sensor inlet air temperature, which is fed to A/D conversion block 122. This particular example embodiment includes an external temperature sensor 132, which feeds a voltage representing ambient temperature to A/D conversion block 120. In many cases, with the two temperature signals coming from the airflow sensor, such an external temperature sensor is not needed since the temperature sensed would be the same as the unheated temperature from the airflow sensor. It can optionally be included however, either for verification of the operation of the airflow sensor, or to provide a local temperature reading in cases where the sampled air is being drawn from a location remote or separate from the air mover, such as from inside a wall with a wall probe. In the embodiment of FIG. 1, controller 118 outputs a binary number to adjust the operating speed of air moving arrangement 102. This number is converted to an analog voltage by a separate digital-to-analog (D/A) converter 134.

Figure 2:
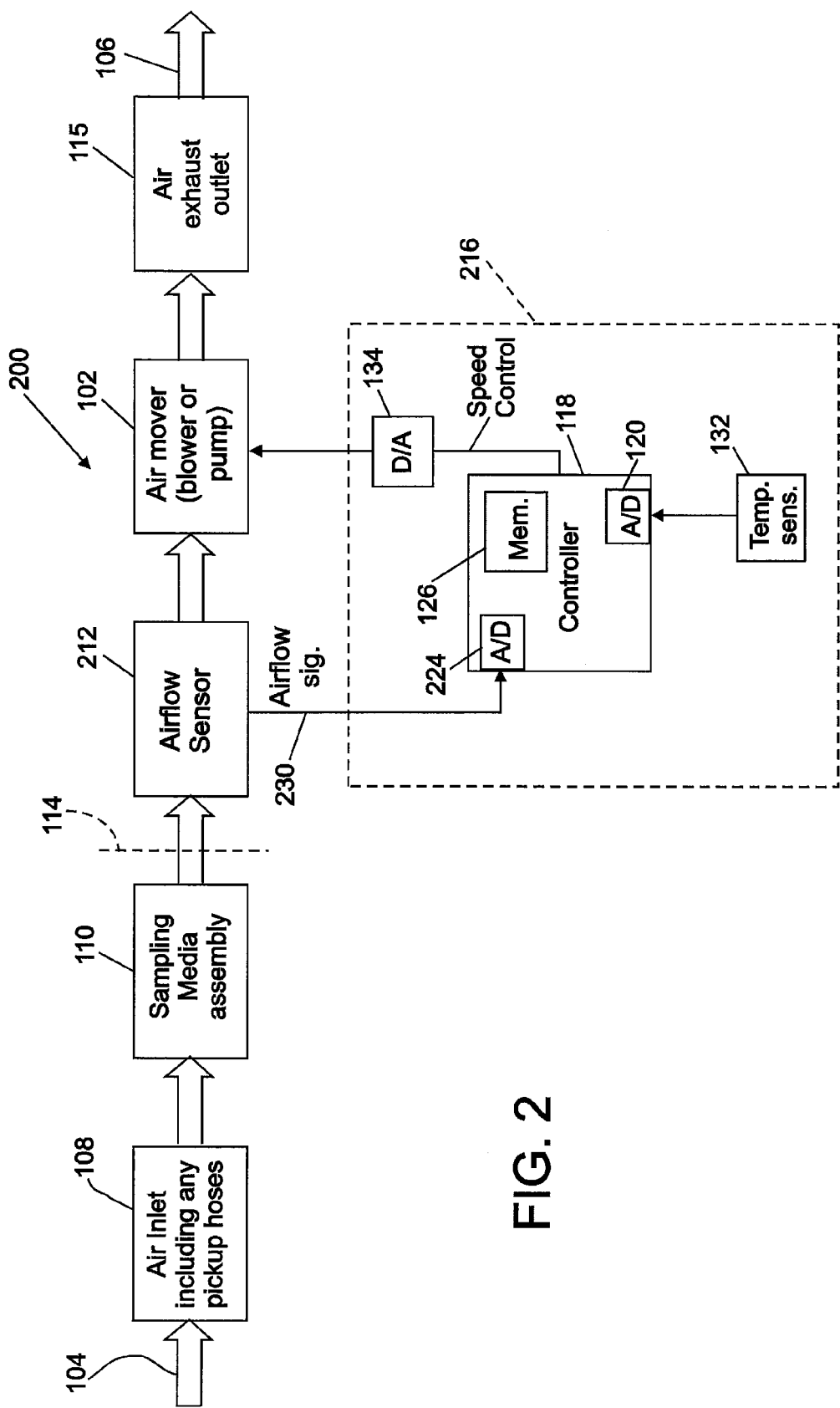
FIG. 2 is a functional block diagram including an air sampler according to another embodiment of the invention.

FIG. 2 illustrates another embodiment of an air sampler according to the present invention. In FIG. 2, many components in the system are identical to those shown in FIG. 1 as evidenced by like reference numbers. However, airflow sensor 212 in this case is a self-contained unit that outputs a voltage signal 230, that is indicative of airflow. Such sensors may be purchased off-the-shelf, and may or may not include integrated inlet and outlet temperature sensors, heaters, and other components necessary to derive an airflow signal. One example of an off-the-shelf airflow sensor that can be used to implement an air sampling system according to an embodiment of the invention is the Honeywell™ AWM720P1 Airflow Sensor, Available from Honeywell, Inc. of Freeport, Ill., USA. Details of how to program the Microchip microcontroller for use with this Honeywell airflow sensor according to an example embodiment of the invention will be discussed later with respect to the flowcharts and lookup table included in the Figures.

Control system 216 of FIG. 2 includes controller 118 as before, but only a single A/D converter block or channel 224, is used to receive the airflow voltage signal that constitutes the signaling from the airflow sensor in this example embodiment. The speed control and external temperature portions of the air sampler of FIG. 2 are identical to the example of FIG. 1, as indicated by the like reference numbers. Note that a sampler like that shown in FIGS. 1 and 2 can be constructed with any of various types of airflow sensors, either self-contained, or constructed from multiple components that work together to measure airflow.

Note that with any of the embodiments of the invention, an internally compensated airflow sensor can be employed that includes digital logic and provides a serial or parallel data stream or similar signaling that is more complex than simple voltages. In such a case, the control system might have to do fewer calculations to compensate for temperature, nonlinearity, null offset, and the like. In fact, significant portions of what is described as the control system in the example embodiments herein, can be included in the airflow sensor instead. The dividing line between the airflow sensor and the control system can thus be in various places without departing from the spirit or scope of the invention. Note also that in addition to the techniques mentioned above, airflow can also be determined by measuring pressure drop across an orifice located within the air stream.

Figures 3, 9:
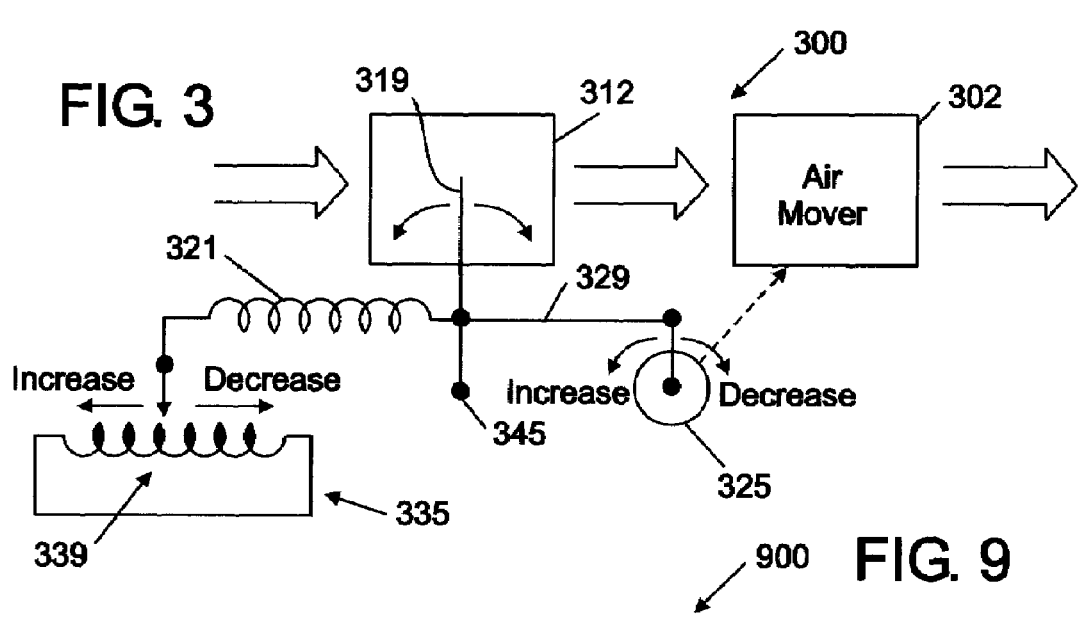
FIG. 3 is a functional block diagram illustrating the operation and construction of a feedback control system according to yet another embodiment of the present invention.
FIG. 9 shows a look-up table that can be used with some controller-based embodiments of the present invention.

FIG. 3 is a conceptual block diagram of another embodiment of an air sampler. FIG. 3 illustrates at least a portion 300, of an air sampler. This particular example illustrates a mechanical feedback control mechanism. Again, in FIG. 3, the arrows indicate the stream. Air moving arrangement 302 can be a fan, pump, or other device as before, including an air moving arrangement that consists of a fan or pump and a valve that adjusts the effective, operating speed or airflow of the air moving arrangement. Airflow sensor 312 in this example uses a mechanical fin 319, the degree of deflection of which indicates airflow. Spring 321 and rod 329, are connected to fin 319 just above pivot point 345. Thus, in this example, a mechanical linkage provides the "signaling" corresponding to airflow. Adjustment device 325 alters the effective speed of air mover 302. Adjustment device 325 can be, for example, a valve control. User input device 335 in this example is a mechanical slider that allows spring 321 to be anchored at any of various physical positions 339 to allow increase or decrease in airflow by indirectly moving adjustment device 325 as indicated in the drawing legends.

Figure 4:
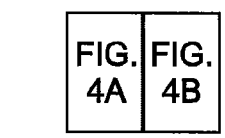
FIG. 4 is a schematic block diagram showing the controller and related components for controller-based embodiments of the present invention. Due to the number of components shown in the diagram, it is split into two parts, FIG. 4A and FIG. 4B.
Figure 4A:
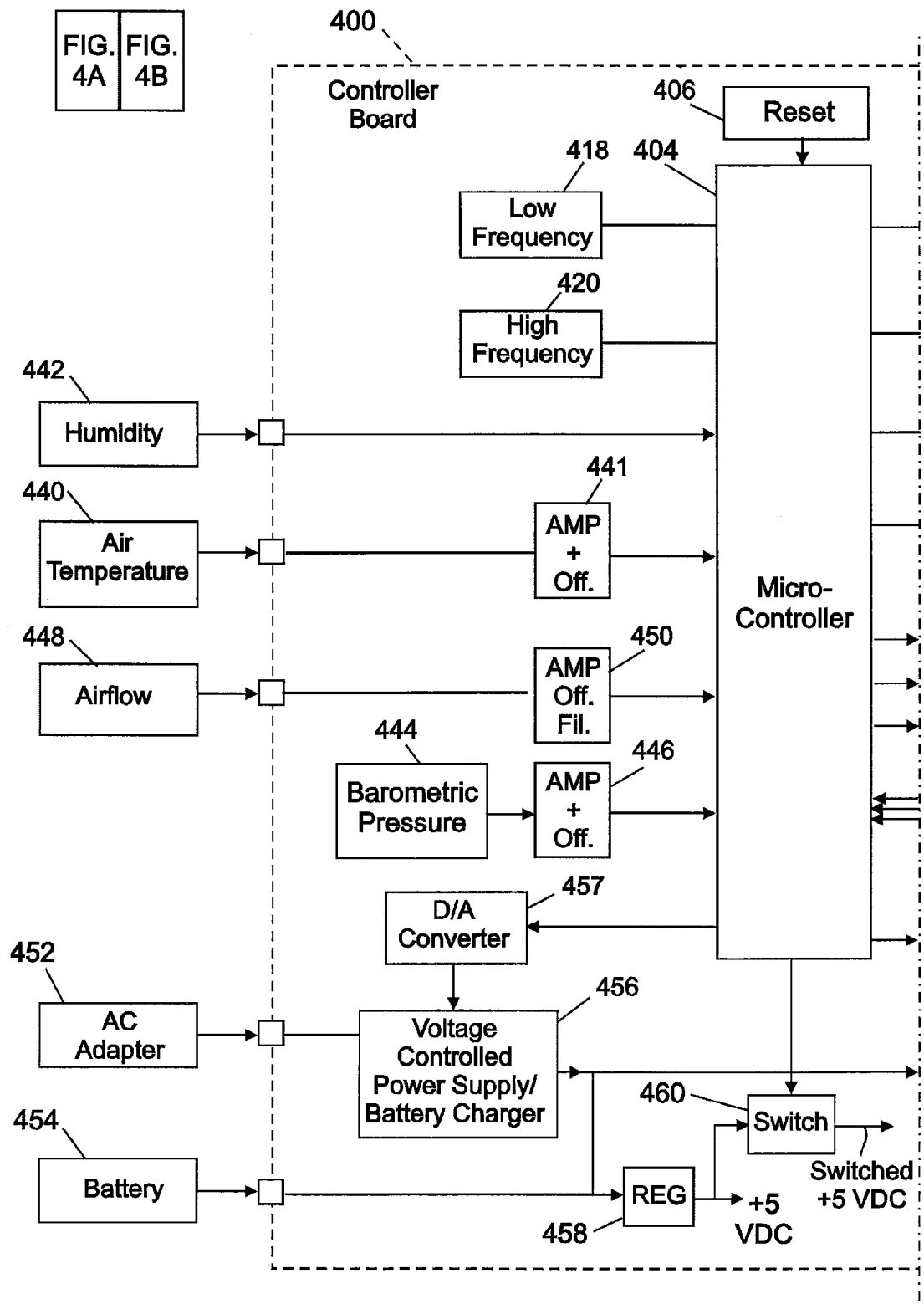
Figure 4B:
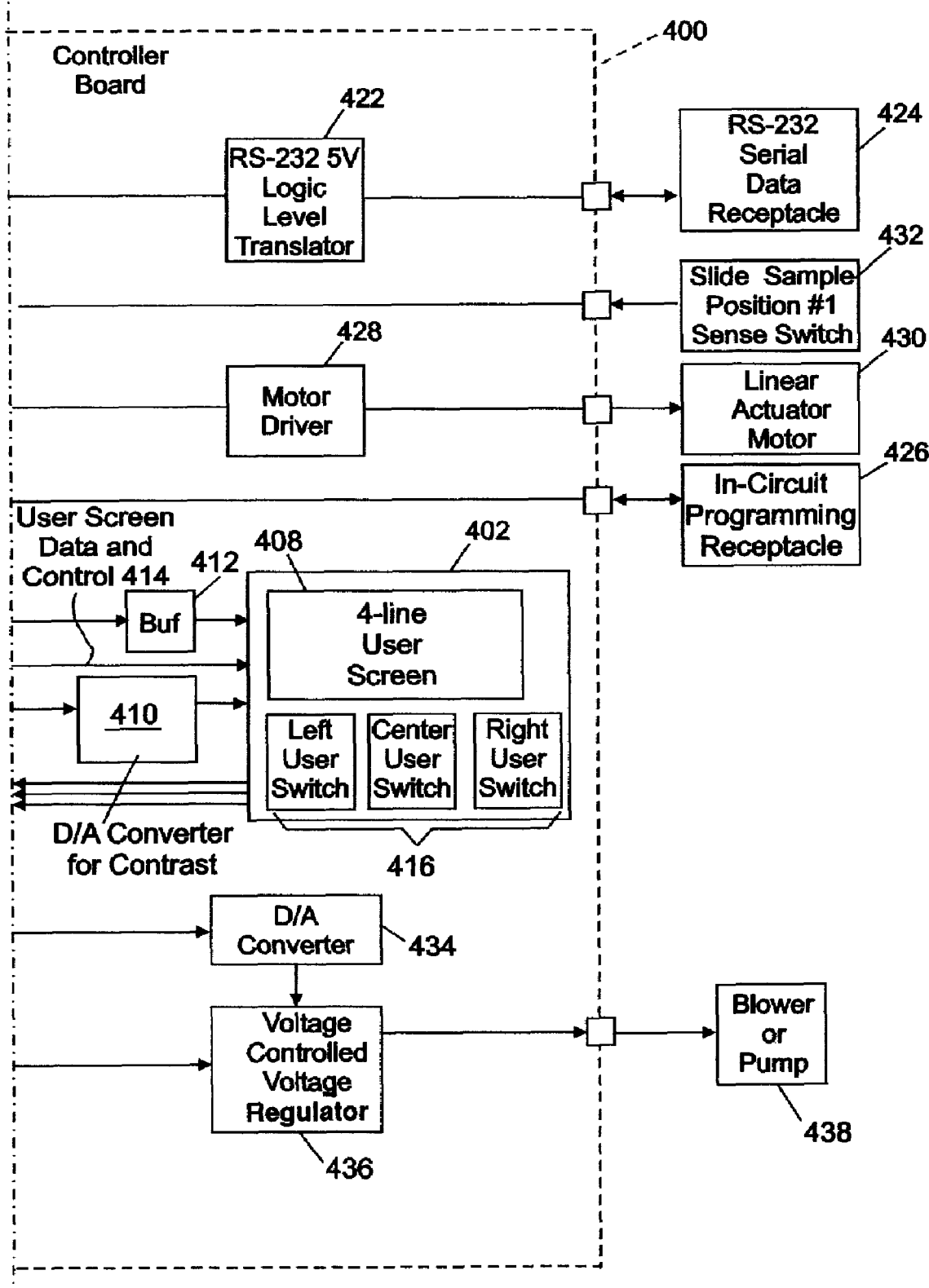

FIG. 4 provides a detailed block diagram showing the construction of a controller board 400, based on the previously mentioned Microchip microcontroller. Because of the number of components shown in this illustration of an example controller board, the diagram is split into two parts, labeled FIG. 4A and FIG. 4B. Such a controller board can be used in the implementation of a control system according to example embodiments of the invention. Note that in this example, the control system implements both an airflow feedback mechanism, and user adjustable airflow, however, an embodiment of the invention might make use of integrated airflow sensing or measurement to implement only one of these features or other features. For convenience, connections to some components that are located within an air sampler according to an example embodiment of the invention, but which are not on the controller board are also shown, along with the components or component groups themselves. Note also that in this example embodiment, a daughter-board 402, is also shown that contains a display. Also note that the terms "controller" and "microcontroller" may be used interchangeably herein.

FIG. 4 includes microcontroller 404 as previously discussed. The microcontroller can be designed to operate anytime it is connected to a battery or other power supply. It can also be programmed to change to a power conserving "sleep" mode when user activity ceases and there are no samples currently running. Once in the sleep mode the microcontroller in this embodiment only wakes up at periodic intervals as necessary to maintain its internal, real-time clock/calendar and check for sample time "wake alarms"; thereafter it immediately goes back to sleep if none are detected. In example embodiments, the microcontroller wakes up and stays awake whenever it senses that a user button has been pressed, or when it determines it is time to take a user programmed, timer activated sample. During this "wake up" event, the user display is switched on and all of the sensors are powered. The microcontroller can be programmed to go back to sleep some preset period of time after the last user button is pressed if no sample is being taken at the time.

The microcontroller used in this example embodiment has an internal, 8 channel, 10 bit A/D converter, which functions the same as eight separate voltmeters, each of which is capable of reading up to 1024 unique voltage values ranging from 0 to 5.0 VDC. Example embodiments of the invention are implemented by using fractional multipliers with a denominator of 256, since dividing by 256 in binary is analogous to dividing by ten in decimal.

Returning to FIG. 4, a reset circuit 406, is provided for microcontroller 404. In addition, the microcontroller includes its own reset circuit, and a so-called "watchdog" timer to reset the microcontroller should it ever become "lost" in its program execution, so that an external reset circuit may not be needed depending on whether there is a desire to provide features, such as low voltage detection (or "brownout detection"), with less power consumption. A four line, liquid crystal display (LCD) user screen 408 is provided in this example. A display device is used in this embodiment that does not provide for direct user adjustability of the contrast or backlight. Microcontroller 404 indirectly adjusts the contrast of the LCD display by controlling the DC voltage to a contrast adjust pin using D/A converter 410. The backlight for the display is controlled by modulating voltage to the display's backlight circuitry using one of the microcontroller's pulse width modulation (PWM) outputs in conjunction with a buffer transistor 412. Of course, normal user signaling for the displayed characters is provided by signal path 414 as is known in the art.

In this example embodiment, three user push button switches 416, are included. These switches are referred to as "soft" switches since their function is dependent upon the user screen displayed at the time pressed. The bottom line of the user screen can be made to label the function of each of the three switches, which are located immediately below the screen. If the display is not active when a switch is pressed, the controller "wakes up" and displays either a main screen or another screen as appropriate.

Microcontroller 404 is connected to low frequency crystal 418 and high frequency resonator 420 to provide appropriate clocking. The controller in this example design has two separate oscillators. An 8 MHz oscillator that is resonator based and another 32.768 kHz that is crystal based. Both oscillators are internal to the microcontroller and have different functions. The 32.768 kHz crystal based oscillator drives a timer/counter internal to the microcontroller and is responsible for generating interrupts to the microcontroller at exactly one-second intervals. This low frequency, low power, oscillator runs anytime the microcontroller is powered; including during "sleep" mode. The 8 MHz resonator based oscillator which consumes more power is only operated when the controller is awake. The use of this 8 MHz frequency gives the processor an instruction cycle time of 8/4=2 MHz. Most, but not all, of the microcontroller's instructions execute in one instruction cycle, so overall performance in this example embodiment is a little less that 2 MIPS.

In this example, the controller has an RS-232 type serial interface which is converted to standard RS-232 levels with level translator 422, which is in turn connected to an RS-232 data receptacle 424. Microcontroller 404 in this example allows for accessing program memory either via the RS-232 type interface, or through an "in-circuit" factory programming receptacle 426. It should be noted that an air sampler could be built with a universal serial bus (USB) interface, a Firewire interface, or even a wired or wireless Ethernet or other local area network (LAN) interface. This interface might be used to exchange either program or data information, or both, between the sampler and the interfaced device.

As previously mentioned, the invention can find use in a variety of types and styles of air samplers and air sampling systems. In the example embodiment shown in FIG. 4, provisions are made for use in a sampler with a self-contained media assembly of the type where a microscope slide is incrementally moved to collect samples at regular intervals. This is the type of sampler described in U.S. Pat. No. 5,201,231, which was previously discussed. In this case, stepper motor driver components 428 are provided to control a linear actuator stepper motor 430, which is used to move the slide from one sample position to another. Similarly, for use in such a sampler, position sense switch 432 is provided to sense the starting position of the slide. With these connections to microcontroller 404, the rotation step angle and number of stepper motor rotations can be precisely controlled by microcontroller 404 so movement of the slide is inherently precise.

D/A converter 434 in the example of FIG. 4 feeds voltage controlled voltage regulator 436 to provide operating speed control to the air sampler's blower or pump 438. Depending on the type and design of the air mover used, the control voltage can actually be the supply voltage for the air mover, or a separate control signal. Other example embodiments for operating speed control include modulating a voltage to vary its duty cycle, and running the fan, pump, or similar device at a constant real operating speed but varying the effective operating speed or airflow of the air moving arrangement by using a voltage to adjust a cutoff or bypass valve to vary the amount of air being moved. For purposes of this disclosure, any discussion of adjusting or changing the "speed" or the "operating speed" includes all of these alternatives.

The system shown in FIG. 4 includes various environmental sensors. It should be noted that not all of these may be required to perform sampling operations, especially if a mass airflow sensor is used as the integrated airflow sensor. In some cases, the sensors can be included to record environmental information in memory for reference. In some cases, an airflow sensor might be used that does not operate accurately outside of certain environmental limits, and the sensors provide a way for the controller to notify an operator when a limit is exceeded. All sensors do not have to be included in every embodiment of an airflow sampler according to the invention. Also, the sensors that are included can be used to compensate for limitations or characteristics of the airflow sensor either through hardware, software, or both.

Temperature sensor 440 is connected to controller 404 through an operational amplifier-based amplification and offset circuit, 441. In some example embodiments, the temperature sensor can be a National Semiconductor™ LM62 temperature sensor available from National Semiconductor Corporation of Santa Clara, Calif., USA. This circuit board mounted sensor outputs a voltage proportional to Centigrade temperature; more specifically, at 0° C. the sensor outputs 480 millivolts and the output increases by 15.6 millivolts for each Centigrade degree. Each A/D converter in controller 404 has up to ten bits of resolution which results in 4.88 millivolts/bit sensitivity with a 5.0 VDC power bus. The amplification and offset circuit 441, is applied to achieve a resolution of 0.1° C. for each A/D converter bit. In this example embodiment, a user calibration routine is provided to ensure accuracy of the measured, external temperature within a window of a few tenths of a degree.

This example embodiment includes a humidity sensor 442, connected to one of the A/D channels of the controller. One example of a humidity sensor that can be used is the Honeywell™ HIH-3610 humidity sensor. With such a sensor, a humidity dependent voltage output ranging from 0.8 to 3.9 VDC is produced. This humidity sensitive voltage level output is affected by changes in temperature and if use is made of such a humidity sensor, the software for the controller should be written to compensate the displayed humidity value using measured air temperature from the external temperature sensor to ensure optimal accuracy. Alternatively, temperature compensation could be provided in hardware.

In the example of FIG. 4, barometric pressure sensor 444 is connected to one of the A/D inputs of microcontroller 404 via amplification and offset circuit 446. One example sensor that can be used to provide barometric pressure indication is the Motorola™ MPXA6115 barometric pressure sensor, available from Motorola, Inc, of Schaumburg, Ill., USA. In one embodiment, in order to provide barometric pressure measurement at altitudes ranging from approximately sea level (29.92" Hg) to 10,000 ft (20.57" Hg) while allowing +/−1.00" Hg for weather, the controller should display a total range of pressure from 29.92−20.57+2.00=11.35 with 0.01" Hg resolution. The resulting 1135 count from the Motorola sensor exceeds the 1024 count resolution of the microcontroller's 10 bit A/D converter. In order to match the output voltage of the barometric pressure sensor to the 0.01" Hg resolution of the A/D converter, amplifier and offset circuit 446 should have a gain of 3.1414. Allowances must also be made for the minimum pressure offset of the sensor, which is specified to vary up 0.133 VDC. The 3.1414 gain multiplied by the 0.417 VDC offset and divided by 4.8828 millivolts per bit results in need for another eighty-five bits on top of the 1135. Since only 1024 bits of resolution are available with a 10 bit A/D converter, a user can only read barometric pressure within a +/−5.00" Hg (+/−500 A/D counts) window both above and below the last user set barometric pressure. Whenever the user sets the barometric pressure, microcontroller 404 iteratively adjusts this offset voltage to barometric pressure sensor amplifier and offset circuit 446 so that the resulting output is approximately half of the available measuring range. Barometric pressure display should then be capable of measuring approximately 5.00" Hg pressure change both above and below the user's last barometric pressure setting.

In the particular example embodiment corresponding to FIG. 4, the air sampler is provided with a self-contained, off-the-shelf integrated airflow sensor 448. In one example, the airflow sensor used is the previously mentioned Honeywell AWM720P1 Airflow Sensor. Amplification and offset circuitry 450 interfaces the airflow sensor to controller 404. Circuitry 450 also includes filtering to remove air mover impulses that can be introduced into the airflow sensor output, in particular, when a pump is used. Further detail of implementing an example embodiment of an air mover according to the invention using this sensor is discussed in relation to the flowcharts which illustrate the operation of an example air sampler, and in relation to FIG. 9.

Controller board 400 contains additional components and connections which relate to powering the various components, although the power supply connections for the controller and related circuits are as is known in the art and are not shown for clarity. Connections are provided for a power supply adapter 452, for optional AC power and battery charging, and for a battery 454. A voltage controlled power supply and battery charger 456, is provided to charge the battery and power the air mover via voltage regulator 436. D/A converter 457 is connected between microcontroller 404 and voltage controlled power and battery charges 456. A 5.0 VDC supply voltage is also provided by voltage regulator 458. A switched 5.0 VDC voltage is provided by switch 460. The switched supply voltage can be used to supply power to components, such as sensors, that can be switched off in order to allow controller 404 and its installed firmware or microcode to better manage the power consumption of the air sampler. Additional features and components can be provided for power and battery management as is known in the art. These might include, among other items, charge status indicator lamps or LED's, a battery disconnect relay, and battery voltage sensing and adjustment circuitry.

Having shown and discussed illustrative embodiments of an air sampler and the control system according to embodiments of the invention, the operation of an example air sampler will now be detailed so that the reader can gain an understanding of the various programming considerations involved in implementing the invention. For purposes of the following discussion of FIGS. 5-9, it can be assumed that the off-the-shelf airflow sensor as described above is being used with the previously discussed Microchip off-the-shelf microcontroller. It cannot be overemphasized that these components are shown by way of example only, and an air sampler can be implemented using any of various combinations of components without departing from the scope of the invention. This generality can be especially appreciated when one considers that other types and models of airflow sensors can produce similar results and may be calibrated and used in a similar way. It can also be assumed that for this example sampler, both an airflow feedback mechanism and a user input device or mechanism to adjust target and/or actual airflow are included in the control system.

The AWM720P1 is a 0-200 LPM airflow sensor. Air samplers of the type being considered herein typically sample at flow rates between 0 and 30 LPM. However, the sensor has a nonlinear output and the range of output voltage over airflow is quite expanded at low airflows. In fact, this sensor outputs approximately half of its maximum net voltage (1.9 of 4.0 VDC) at 25 LPM. Nevertheless, amplification and offset circuitry as discussed relative to FIG. 4 is used in order to improve measurable resolution from the sensor. In example embodiments this circuitry includes an operational amplifier that amplifies the 1.0 to 5.0 VDC output voltage from the sensor by factor of approximately two and then shifts the 0 LPM offset voltage from 1.0 to approximately 0.5 VDC. This amplification and offset effectively doubles the microcontroller's A/D converter's resolution over what it would be without the amplification and offset. Filtering is also added as previously discussed. In at least one embodiment, this filtering can be implemented with capacitors. Additional filtering can be provided by software if needed. Throughout the rest of this disclosure, when the airflow sensor output voltage or signal is referred to, what is meant may be the output signal from the amplification and offset circuit with the filter, not necessarily the output from the airflow sensor.

With respect to the method of operating an air sampler in example embodiments with the Honeywell airflow sensor and the Microchip controller, the airflow readings may still need to be calibrated. In some embodiments, target airflow is preset at a standard value which cannot be changed by a user. In such a case, it is unimportant that the real-time airflow measured by the controller be accurate, except at the normal sampling airflow. All that must be known is whether the actual airflow drifts from a stored, target value, and when and whether it has been brought back in line with the stored value. However, some calibration may still need to be performed to achieve accuracy at the fixed airflow rate. Such calibration could be performed either when the sampler is manufactured, or in the field. In other embodiments, a user can set an adjustable sampling airflow, so that calibration for accuracy is more important. Note that the ability of a user to set a sampling airflow relatively accurately can be included in a sampler either as a stand-alone feature, or together with airflow feedback, in which case the airflow the user sets can also be the stored, target airflow. In embodiments with user adjustable airflow and/or, where the airflow is displayed, the airflow readings as measured by the microcontroller need to be relatively accurate, so additional calculations may be needed to correct for the linearity characteristic of the airflow sensor. This process might also be called linearization or non-linear compensation. The use of the term "linearity characteristic" is not meant to imply that the airflow sensor is linear, but rather that the characteristic curve of voltage output (either direct or compensated by amplification and/or offset) vs. airflow, may or may not be linear. In either case, calculations may be necessary to correct for at least one current environmental reading; in the examples, external temperature.

Figure 5:
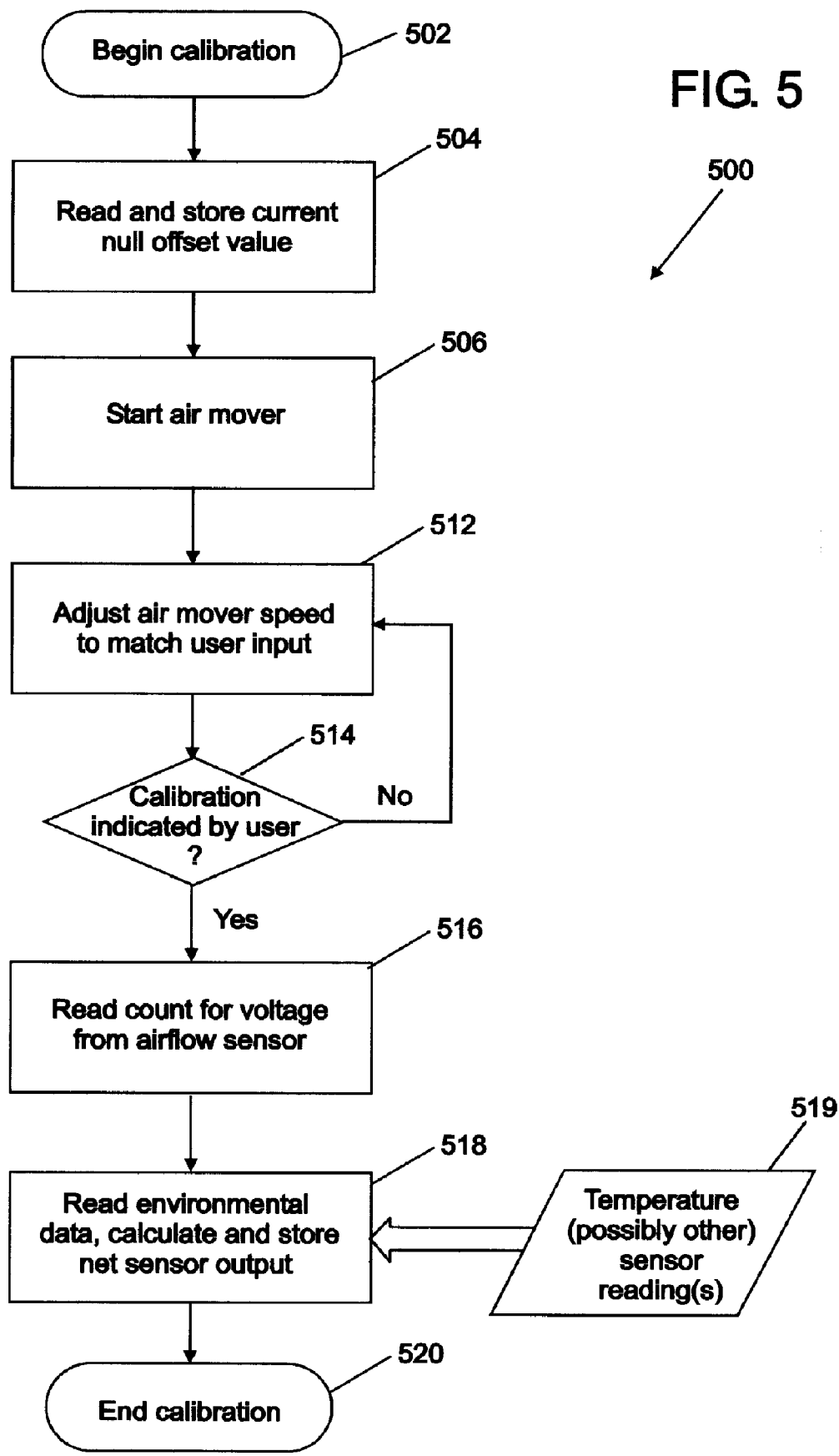
FIG. 5 is a flowchart illustrating a method according to some example embodiments of the present invention.
Figure 6:
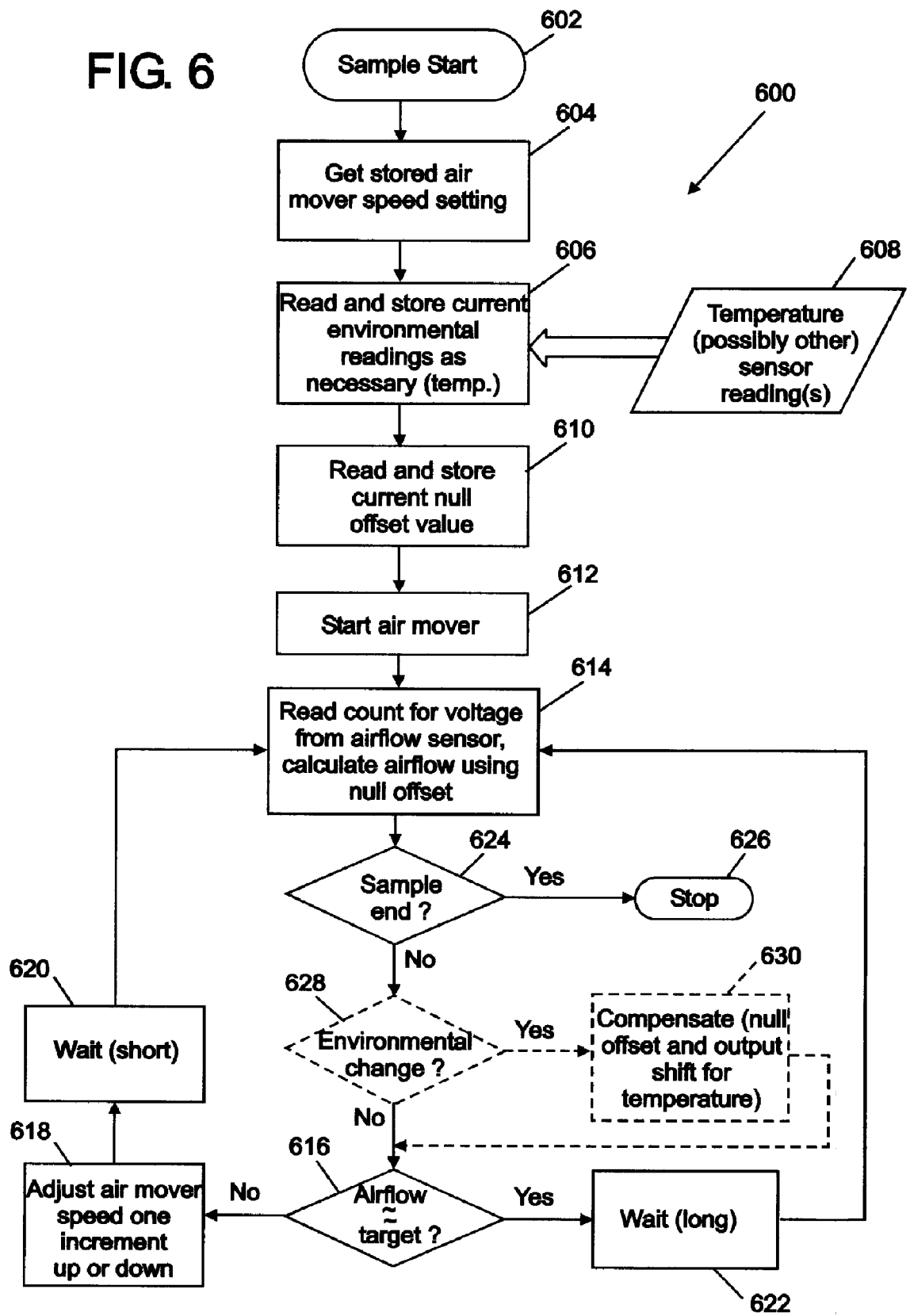
FIG. 6 is a flowchart illustrating another method according to some example embodiments of the present invention.
Figure 7:
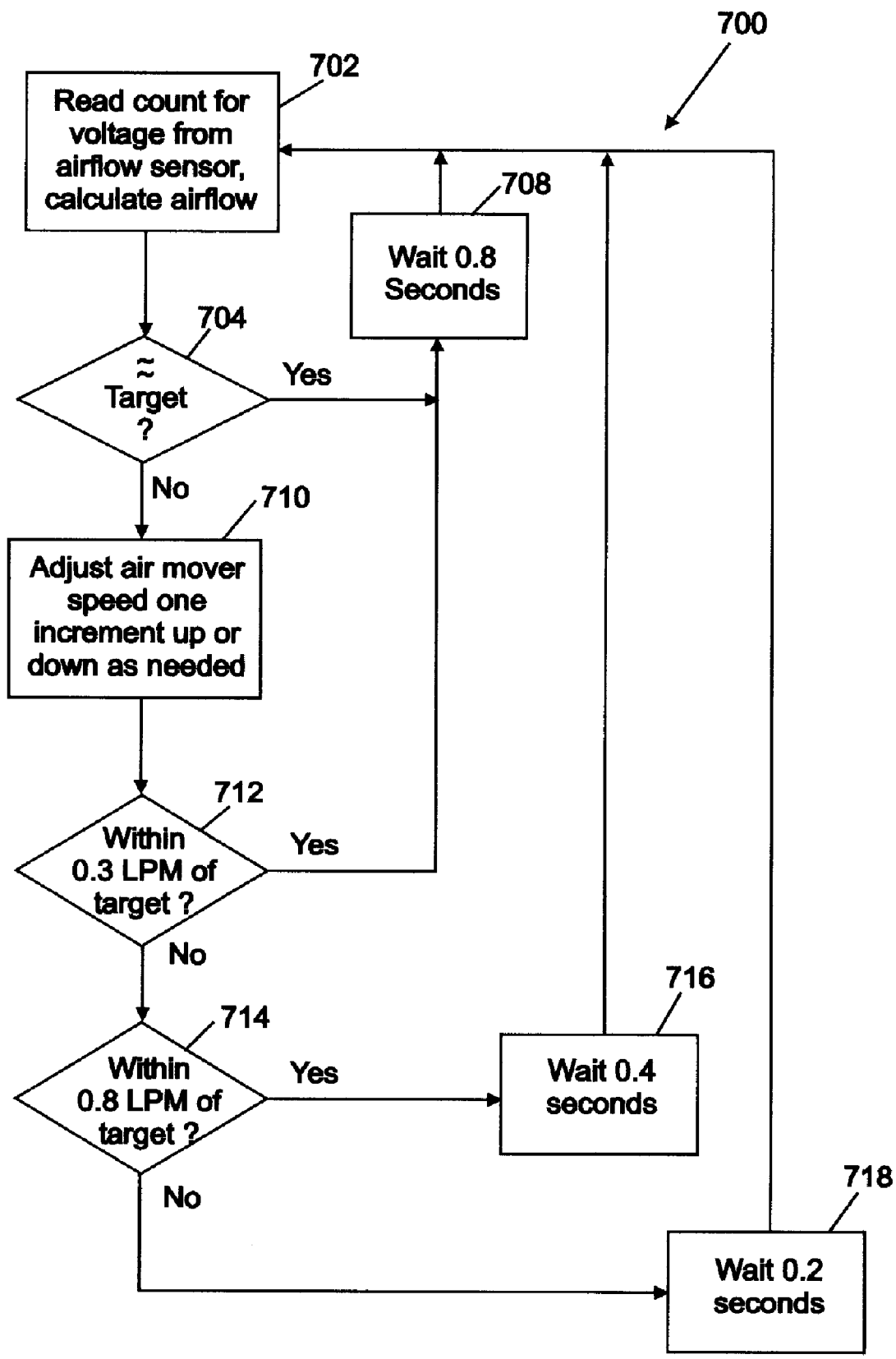
FIG. 7 is a flowchart illustrating further detail of some of the processes shown in the flowchart of FIG. 6.
Figure 8:
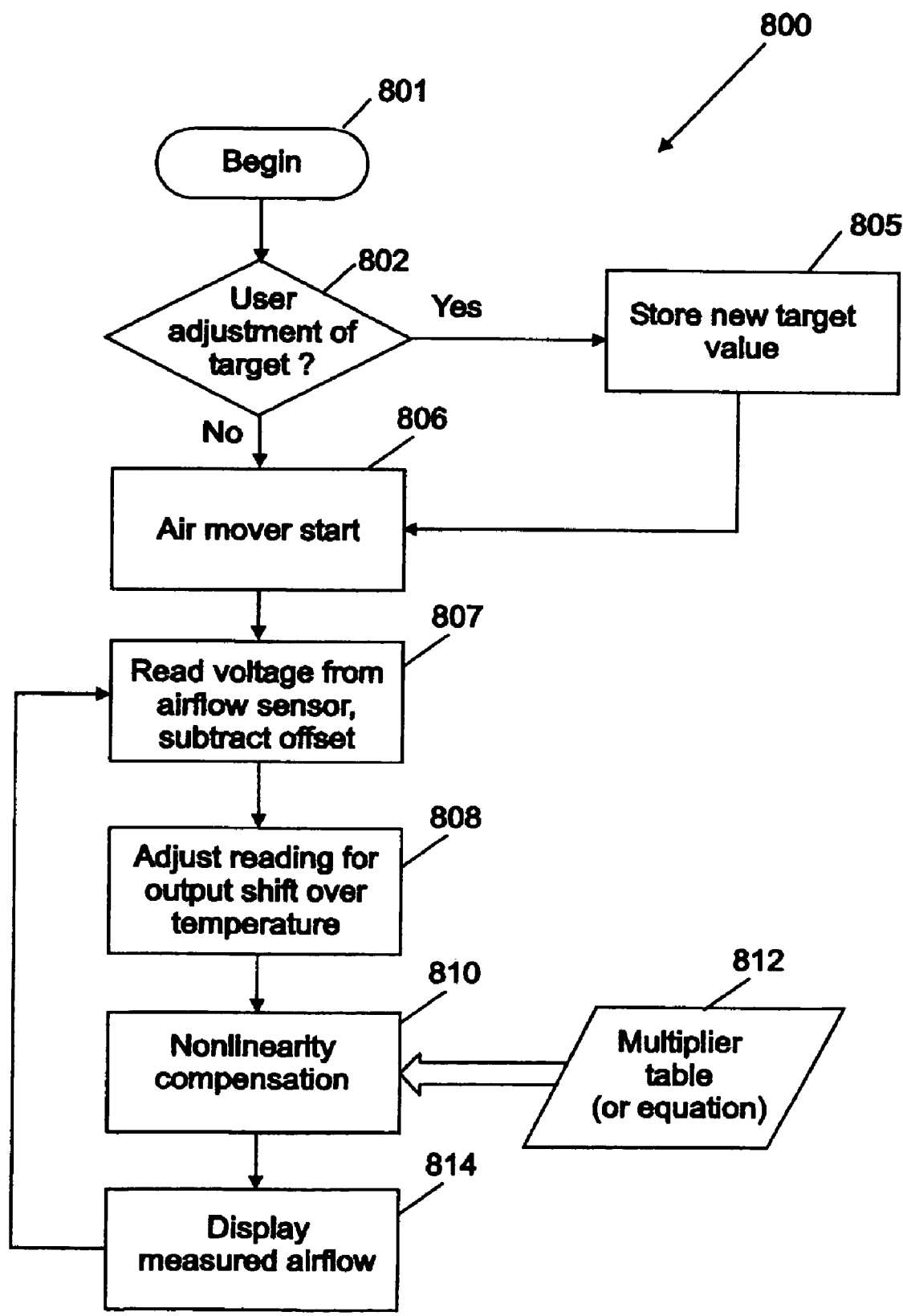
FIG. 8 is a flowchart illustrating another method according to some example embodiments of the present invention.

FIG. 5 illustrates a process by which the air sampler can be calibrated prior to taking any readings, as may be needed with either an adjustable or fixed target airflow value sampler. FIGS. 6 and 7 illustrate the airflow feedback process which is applied to both fixed and adjustable airflow samplers using airflow feedback. FIG. 8 illustrates the process for user adjustable target airflow to be set in an air sampler having airflow feedback. FIG. 9 illustrates airflow sensor nonlinearity compensation. All flowcharts are drawn in the typical fashion, with process steps and/or sub-processes being illustrated as a series of process blocks.

In the example embodiments, there are two airflow sensor parameters that must be separately temperature compensated as part of a calibration process, "null offset" and "output shift-with-temperature." The Honeywell airflow sensor requires approximately one second of warm-up time. However, if it is powered up whenever the user display is activated, this warm-up time is inherently provided, since a user cannot execute the menu steps to initiate operation faster than that. The DC voltage output by an airflow sensor at 0 LPM is referred to as the "null voltage" or "null offset voltage." It is approximately 1.0 VDC at the output of the sensor in the case of the Honeywell sensor and 0.5 VDC at the output of the amplifier/offset circuitry in the example embodiment. This "null voltage" fluctuates up and down with temperature and unless compensated for in software/firmware (or hardware), may adversely affect sensor data, especially at low airflows.

In the example embodiments, the controller software always reads the "no airflow" output voltage of the airflow sensor after warm-up and immediately before the air mover is operated when the actual airflow is known to be 0.0 LPM. This process occurs for both calibration and sampling. In process 500 of FIG. 5, calibration begins at block 502, and the null offset value is read and stored at block 504.

This null offset voltage now becomes the 0 LPM reference voltage. As will be seen, this null offset voltage is also read and stored immediately prior to a sampling period to compensate for temperature changes. Any changes in the null offset that occur between sampling periods are automatically accommodated. If there is a desire to accommodate the possibility of the temperature changing during a sampling period, a null offset temperature compensation table or equation can be built into memory. Alternatively, each unit can be temperature calibrated in advance at two temperature extremes and linearity at temperatures between the two can be assumed. Another alternative would be to have the air sampler firmware switch off the air mover at periodic intervals within a sample period to reread the null offset voltage.

Returning to FIG. 5, during calibration, the air mover is started at block 506. The air sampler goes into a user adjustment mode at block 512, where instructions are displayed on a user display device, in the example embodiments, the LCD screen. The instructions tell the user to push the buttons, supplying user input to manually adjust air mover speed as necessary to achieve "calibration" airflow; which may be a fixed, stored, target value, such as 15 LPM or 28.3 LPM (1 CFM). Note that on a sampler with adjustable target airflow it is best to calibrate airflow at or near the sampler's maximum airflow regardless of value, whereas on a sampler without an adjustable target, the unit should be calibrated at its fixed target airflow value. At block 514, the user indicates calibration by pressing a button, and the controller reads the count for the airflow sensor at block 516.

Separate from the null offset voltage temperature variation, there is another temperature sensitivity characteristic of some airflow sensors called "output shift-with-temperature" where the sensitivity of the sensor (output voltage as a function of airflow) changes with temperature. In the case of the Honeywell sensor, the optimal temperature is considered 77° F., and the change is mostly linear and amounts to a decrease of about 2% of reading going from 77 to 50 degrees F. and an increase of about 2% of reading going from 77 to 104 degrees F. In the example embodiments, the external temperature sensor for the air sampler can be used to determine an effective output that includes the effects of output shift-with-temperature. Thus, external temperature is read and compensated for at block 518 of FIG. 5, the reading coming from the temperature sensor as illustrated by input block 519. In some alternate embodiments, it may be necessary to provide compensation based on other environmental readings as noted in block 519, or possibly none at all. The controller provides linear compensation in the case of the Honeywell, integrated airflow sensor, centered around 77° F. Although compensation accuracy is reduced outside of the range of 50-104 degrees, enough accuracy for good results can be achieved with such a scheme even outside of this range.

A number ranging from 0-1023 that is representative of the 77 degrees F. output voltage of the airflow sensor at the specified calibration airflow value less the "null offset voltage" is then calculated and stored in non-volatile memory at block 518. This number can be referred to herein as the temperature compensated "span." A number proportional to air moving arrangement speed is also saved in non-volatile memory and is subsequently used as the starting operating speed of the air moving arrangement. This stored number allows the air moving arrangement to begin operating at the beginning of each sample at a speed that is very close to the speed it will be running at as a result of airflow feedback. Process 500 ends at block 520.

As an example temperature compensated span calculation, assume the null offset voltage from the airflow sensor amplifier is 0.50 VDC. The corresponding A/D converter value will be 0.50 volts / 4.8828=102. Also assume that the amplified voltage from the airflow sensor at 15 LPM is 4.12 VDC. The corresponding A/D converter value will be 4.12 volts/4.8828=843. This means the unadjusted airflow sensor span (0 to 15 LPM voltage differential) is 843−102=741. Let's also assume that calibration was performed at 63.5 degrees F. Sensitivity is reduced linearly by 2% over 27° F. referenced to 77° F. Thus, the span is less than would be if the unit had been calibrated at 77° F. The span should be adjusted. Since the output from the sensor is low by 2% for every 27° F., in this example the temperature is down 13.5° F. Thus, the measured calibration span is about 1% less than it would be at 77° F. To compensate, the controller firmware adjusts the earlier 741 span figure to get a value of 748 which approximately 1% higher. This resulting adjusted value is saved in non-volatile memory as the "temperature compensated airflow sensor span calibration data value." It represents the 0-15 LPM microcontroller A/D converter span count at 77° F.

FIG. 6 is a flowchart style diagram illustrating an airflow feedback process 600, according to example embodiments of the invention. In typical use, an air sampler runs for a plurality of "sample periods" to collect samples to be analyzed. The flowchart of FIG. 6 illustrates the process of providing airflow feedback for a single sample period. The process can repeat for each sampling period. The sample starts at block 602. When a sample is started, the air moving arrangement begins running either at the calibration speed stored in non-volatile memory at the time of calibration, or an operating speed saved in memory at the end of the previous sample. The former can be used in the case of the first sample after setup. For the remainder of the samples, either value can be used. This choice can be implemented as a user setting via a menu, or the choice can be permanently programmed into the air sampler. In either case, the stored setting is retrieved from memory at block 604. The objective is to start the air moving arrangement running at a speed close to what it will be when operating in feedback. At blocks 606, 608, and 610, null offset information can be updated to account for changes in environmental readings, such as temperature, during the off period between samples, or during any time that has elapsed since calibration if this is the first sample. These steps can be performed in essentially the same way as they were during calibration. The air moving arrangement starts at block 612.

It should be noted that in some embodiments, the environmental data read in block 608 (temperature, humidity and barometric pressure) prior to starting the "air mover" is data that is saved in a "history" memory for possible future reference by the operator or user. The temperature data used for airflow sensor compensation is repeatedly read during the sampling just like the airflow sensor signaling itself. Thus, the sensor's "output shift-with-temperature" parameter is constantly being compensated for with actual rather than stored temperature data. The history memory can be a non-volatile memory for storing a history of environmental and sample related data. Sample related data can include, for example, date, time, sampling time, airflow and a sample number in cases where a slide contains multiple samples.

The remaining process blocks of FIG. 6 represent processes that are performed continuously during the sample, notwithstanding the fact that for clarity they are illustrated in a specific sequence. At block 614 the count from the integrated airflow sensor is read and an actual, current airflow is calculated using stored data for null offset. Jumping to decision block 616, if the airflow has moved too far away from the target airflow, the air moving arrangement operating speed is adjusted at block 618, and a waiting period is applied at block 620 before making any further adjustments based on current readings. As will be described below with respect to FIG. 7, the length of the waiting period may be made dependent on how far away from the target the measured airflow is, as determined by calculations performed based on the read at block 614 and temperature compensation at block 630. If the airflow is on target, just a waiting period is applied at block 622, which, in this embodiment, is longer than the length of the any waiting period applied at block 620.

During the sampling process, a timer is monitored by the microcontroller at block 624 to determine if it is time to end the current sample. If so, the sample ends and the air moving arrangement is shut off at block 626. Compensation for airflow sensor output shift-with-temperature is ongoing and illustrated in blocks 628 and 630. Optionally, if the environmental change is great enough, the air moving arrangement is stopped and the "null offset" shift-with-temperature is also compensated for at block 630. An alternative method would be to have the software know how the null shift-with-temperature of the airflow sensor changes with temperature and compensate with software. If the null shift-with-temperature is predictable from sensor to sensor, then either a lookup table or equation could be used to automatically compensate while sampling since the controller knows how much the temperature has changed since the sample was started. If the null shift is not predictable from sensor to sensor, then a factory calibration process could be used where the null offset of the sensor is read and stored for both a low and a high temperature with the assumption that it is somewhat linear in between. Note that this calibration procedure may require that the sampler be operated at two temperature extremes as part of the calibration process.

FIG. 7 breaks out in further detail, an example subprocess, 700, of the feedback process itself. The actual, temperature compensated, current airflow is being calculated based on sensor voltage at block 702. Measured airflow is then compared with target airflow at block 704. If measured airflow is substantially equal to target airflow at block 704, no air mover speed adjustment is made and there is a waiting period of 0.8 seconds imposed at block 708 before calculating and comparing airflow again. If instead the airflow has drifted from the target airflow, then the air moving arrangement speed count is either incremented or decremented by one (1 of 256) as needed at block 710, and a determination is made at block 712 as to whether the airflow is within 0.3 LPM of the target. If yes, the 0.8 second wait at block 708 is imposed before calculating and comparing again. If instead the difference between measured airflow and target airflow is more than 0.3 LPM, then a determination is made at block 714 as to whether the measured airflow is within 0.8 LPM of the target. If so, a waiting period of only 0.4 seconds is imposed at block 716 before calculating and comparing again. If not, that is, if the measured airflow is more than 0.8 LPM away from the stored, target airflow, a waiting period of only 0.2 seconds is imposed at block 718, and then the airflow is calculated and compared again at block 702.

The threshold and delay values above have been found to work well with samplers that use a pump as the air mover, and that use the Honeywell integrated airflow sensor. Different values and numerous, different algorithms may also work with this and other configurations. It is also possible to adjust these values based on operating conditions and/or the selected airflow in an air sampler with user adjustable target airflow.

The calibration and feedback methods illustrated above are all that is needed for accurate operation of an air sampler that always operates at a fixed, standard airflow rate. However, it is possible to employ the airflow feedback invention in an air sampler with a user-programmable, adjustable, target airflow. As discussed above, in example embodiments, span and null offset calculations are performed to compensate linearly for null offset and output shift-with-temperature. These calculations result in accuracy at a single, stored, calculated value; however, if a user adjusts the stored, target value to operate the air sampler at another flow rate, or if there is a desire to display flow rate accurately, compensation may be needed for nonlinearity in the response curve of the integrated airflow sensor.

A process 800, of a user changing the stored, target value for desired airflow on an air sampler using a menu-driven user interface with soft keys is illustrated in the flowchart of FIG. 8. In practice, this process could be executed concurrently with, or as part of, the process of FIG. 6. The process begins at block 801. At block 802, a check is made as to whether the user has input a target value. If so, the new target value is stored at block 805. At block 806, the air mover starts. The amplified voltage from the airflow sensor is read and the null offset is subtracted at block 807. The reading is adjusted for the span based on the output shift-with-temperature at block 808. Since the airflow is now at a different place on the airflow sensor sensitivity curve, nonlinearity compensation is added or subtracted at block 810. In example embodiments, this is done using input from a multiplier table or a calculation based on an equation as shown at block 812. Measured airflow is displayed at block 814. Normal operation ensues, in which the processes of blocks 807-814 are carried out every time the airflow is read.

As noted earlier, the output of voltage from the Honeywell airflow sensor is not linear as a function of airflow. In the example embodiment using the Honeywell airflow sensor and the Microchip controller, linearization can be accomplished using lookup table 900 shown in FIG. 9. The nominal voltage output of the Honeywell airflow sensor as a function of airflow is curved rather than linear. The curve can be described by the following equation at nominal operating temperature, where Y is airflow sensor output voltage in VDC and X is airflow in LPM.

$$Y(X) = a + bX + cX^2 + dX^3 + eX^4 + fX^5$$

where
a=1.02
b=0.104
c=$-1.43 \times 10^{-3}$
d=$1.11 \times 10^{-5}$
e=$-4.49 \times 10^{-8}$
f=$7.17 \times 10^{-11}$.

Microcontrollers have somewhat limited internal hardware capability for doing arithmetic. Although software can be written to perform what is often referred to as floating point calculations; an alternative method for this example embodiment is to create a lookup table based on the polynomial equation above and have the microcontroller use this lookup table data instead of performing numeric calculations associated with the polynomial equation. An example lookup table 900, based on the above equation is illustrated in FIG. 9.

In this example, representative data for the Honeywell sensor was normalized for an airflow of 15 LPM which is a common, standardized airflow value used for many air samplers and fractional multipliers were then calculated and recorded for airflows ranging from 0 to 20 LPM in 1 LPM increments. The purpose of each of these multipliers is to provide a means for correcting the non-linear output of the airflow sensor at 1 LPM increments. Each of these fractional multipliers was purposely chosen to have a single common denominator of 256 since this is an optimal value for performing binary arithmetic.

If the airflow sensor were linear and the unit had been calibrated at 15 LPM, one would expect the net voltage output by the sensor (net=actual−null offset) at 1 LPM to be exactly $\frac{1}{15}$ of its net voltage at 15 LPM. The Honeywell sensor used in the example embodiments described herein is non-linear and the voltage output by the sensor is actually higher than it would be if it were linear. Based on manufacturer's specification, the net voltage output by the sensor at 1 LPM is 0.093 VDC. Since the sensor outputs a net voltage of 1.313 VDC at 15 LPM, one would have expected a net voltage of 1.313 times ($\frac{1}{15}$)=0.08753 had the sensor been linear. Since it is not linear the actual reading is 0.093/0.0875=1.062857 times the desired reading. It would be possible to correct or linearize this same data by multiplying by the actual sensor data at 1 LPM by the inverse of 1.062875=$\frac{1}{1.062875}$ to compensate. If one converts $\frac{1}{1.062875}$ to a fraction having a denominator of 256, the result is ($\frac{1}{1.062875}$) times 256=240.86 which rounds to 241. Note that this is the number stored for 0-1 LPM value in table 900 of FIG. 9. The remaining tabular data illustrated in Table 900 FIG. 9. was generated using the same technique. Sensor data was not available from Honeywell for airflow between 11 and 14 LPM, inclusive, so a plot was generated that allowed for reasonable estimation of the data values.

This 241 lookup table data value can be checked by multiplying the 0.093 value output by the airflow sensor at 1 LPM by 241/256. 241/256 times 0.093=0.08755 which very closely approximates the 0.08753 linear data value calculated above. Note that the zeros are stored for the fractional multiplier for 0 and 15 LPM. These are two instances where the multiplier is really 256 and 256 is one digit too big to store in a one byte memory location. Only values ranging from 0-255 can be stored in a single byte. In this example embodiment, the software has been written to functionally treat these zeros as 256.

Note also that multipliers for airflow values above 15 LPM are smaller numbers. In this embodiment, these are again treated as special cases where the fractional multiplier is actually greater than 256. For example, the multiplier for 20 LPM is 16 which means (256+16)/256=1.0625. According to the data supplied by Honeywell, the sensor outputs a net voltage of 1.645 at 20 LPM. 1.645 times 1.0625=1.7478 linearized. Since it is known in this example that 15 LPM=1.313 volts. (1.7478/1.313) times 15 LPM=19.967 LPM which rounds to 20.0 LPM which is what is expected.

For even greater accuracy, iteration can be used between the look-up table values. For example, the multiplier jumps from 241 to 221 going from 1 to 2 LPM. The A/D converter divides the measurable range into several hundred counts. Even with just 200 counts over a 0 to 20 LPM measuring range, the microcontroller has resolution to approximately 0.1 LPM, and higher resolution can be provided with greater counts. Therefore, rather than use a constant linear correcting multiplier to convert all measurements between table entries, the firmware iterates between the two known 1 LPM increment data values. For example, assume a non-corrected airflow reading of 1.2 LPM. The microcontroller knows that the 1 LPM correction multiplier is 241 and that the 2 LPM multiplier is 221. The difference between 241 and 221 is 20. Multiplying this difference by 0.2 (1.2 minus 1.0) produces a value of 4. The microcontroller knows that the multiplier data is descending here so it subtracts the 4 from 241, which results in an adjusted multiplier of 237, which is what it uses as a multiplier to linearize the data. Thus, the air sampler can accurately measure airflow at various airflow values, allowing for user adjustment of the stored, target value for airflow feedback and/or a relatively constant and stable operating airflow of the air sampler. Regardless of technique, linearization may be necessary if there is a desire to display accurate, measured airflow while sampling, regardless of whether the target airflow is adjustable.

It should be noted that it is possible to obtain airflow sensors with built-in linearization circuitry. If such a sensor is used, it may be possible to eliminate the linearization from the internal software or firmware of the air sampler.

Specific embodiments of an invention are described herein. One of ordinary skill in the air sampling and electronics arts will quickly recognize that the invention has other applications in other environments. Many embodiments are possible, and the following claims are not intended to limit the scope of the invention to the specific embodiments described above.

What is claimed is:

1. An air sampler comprising:
   an air moving arrangement disposed to be operable to move air over a sampling media, the air moving arrangement having an adjustable operating speed;
   an integrated airflow sensor disposed to be in fluid communication with the air moving arrangement; and
   a control system interfaced to the air moving arrangement, the control system operable to determine a measured airflow based at least in part on signaling from the integrated airflow sensor and a linearity characteristic of the integrated airflow sensor.

2. The air sampler of claim 1 wherein the control system further comprises a feedback control mechanism to maintain the measured airflow substantially in accordance with a target value.

3. The air sampler of claim 2 wherein the control system further comprises a controller disposed to receive the signaling and adjust an operating speed of the air moving arrangement based at least in part on the signaling and the linearity characteristic of the integrated airflow sensor.

4. The air sampler of claim 3 wherein the signaling comprises signals from two temperature sensors disposed within an air stream, wherein a difference in temperature indicated by the signals is indicative of airflow.

5. The air sampler of claim 3 wherein the signaling comprises a voltage which is indicative of airflow.

6. The air sampler of claim 3 wherein the signaling comprises a data stream.

7. The air sampler of claim 3 further comprising an external temperature sensor connected to the controller, and wherein the controller is operable to determine the measured airflow at least in part also based on an external temperature reading.

8. The air sampler of claim 7 further comprising an integrated sampling media assembly disposed to be in fluid communication with the integrated airflow sensor and the air moving arrangement.

9. The air sampler of claim 3 further comprising a user display device connected to the controller operable to display the measured airflow.

10. The air sampler of claim 9 wherein the control system is further operable to determine standard airflow from the measured airflow and the linearity characteristic of the integrated airflow sensor.

11. The air sampler of claim 9 wherein the control system is further operable to store a history of environmental and sample related data.

12. The air sampler of claim 3 further comprising a user input device connected to the controller, and wherein the controller is further operable to adjust the target value based on user input.

13. The air sampler of claim 12 further comprising an external temperature sensor connected to the controller, and wherein the controller is operable to determine the measured airflow at least in part also based on an external temperature reading.

14. The air sampler of claim 13 further comprising an integrated sampling media assembly disposed to be in fluid communication with the integrated airflow sensor and the air moving arrangement.

15. The air sampler of claim 3 further comprising an integrated sampling media assembly disposed to be in fluid communication with the integrated airflow sensor and the air moving arrangement.

16. The air sampler of claim 3 wherein the control system is further operable to determine standard airflow from the measured airflow and the linearity characteristic of the integrated airflow sensor.

17. The air sampler of claim 3 wherein the control system is further operable to store a history of environmental and sample related data.

18. The air sampler of claim 2 wherein the signaling is provided at least in part by a mechanical linkage.

19. The air sampler of claim 2 further comprising an integrated sampling media assembly disposed to be in fluid communication with the integrated airflow sensor and the air moving arrangement.

20. The air sampler of claim 1 wherein the control system further comprises a user input device to adjust the target airflow in response to user input.

21. The air sampler of claim 20 wherein the signaling comprises signals from two temperature sensors disposed within an air stream, wherein a difference in temperature indicated by the signals is indicative of airflow.

22. The air sampler of claim 20 wherein the signaling comprises a voltage which is indicative of airflow.

23. The air sampler of claim 22 further comprising an integrated sampling media assembly disposed to be in fluid communication with the integrated airflow sensor and the air moving arrangement.

24. The air sampler of claim 20 wherein the signaling is provided by a mechanical linkage.

25. The air sampler of claim 20 wherein the signaling comprises a data stream.

26. The air sampler of claim 25 further comprising an integrated sampling media assembly disposed to be in fluid communication with the integrated airflow sensor and the air moving arrangement.

27. The air sampler of claim 20 further comprising an external temperature sensor connected to the controller, and wherein the controller is operable to determine the measured airflow at least in part based on an external temperature reading.

28. The air sampler of claim 27 further comprising an integrated sampling media assembly disposed to be in fluid communication with the integrated airflow sensor and the air moving arrangement.

29. The air sampler of claim 20 further comprising an integrated sampling media assembly disposed to be in fluid communication with the integrated airflow sensor and the air moving arrangement.

30. The air sampler of claim 1 wherein the control system is further operable to determine standard airflow from the measured airflow and the linearity characteristic of the integrated airflow sensor.

31. The air sampler of claim 1 wherein the control system is further operable to store a history of environmental and sample related data.

32. A method of adjusting an operating speed for an air moving arrangement in an air sampler having an integrated airflow sensor, the method comprising:
   calculating a measured airflow based, at least in part on a linearity characteristic of the integrated airflow sensor, and on at least one of, signaling from the integrated airflow sensor, a null offset value for the integrated airflow sensor, and a current environmental reading;
   comparing the measured airflow to a target value to obtain a result; and
   adjusting the operating speed of the air moving arrangement based on the result to maintain the measured airflow substantially in accordance with the target value.

33. The method of claim 32 further comprising displaying the measured airflow.

34. The method of claim 32 further comprising changing the target value in response to user input.

35. The method of claim 32 wherein the calculating of the measured airflow is also accomplished based in part on a current environmental reading comprising an external temperature reading.

36. The method of claim 34 wherein the calculating of the measured airflow is also accomplished based in part on a current environmental reading comprising an external temperature reading.

37. Apparatus for adjusting an operating speed for an air moving arrangement in an air sampler to maintain a measured airflow, the apparatus comprising:
   means for sensing airflow;
   means for calculating a measured airflow based, at least in part on a linearity characteristic of the integrated airflow sensor, and on at least one of, signaling from the integrated airflow sensor, a null offset value for the integrated airflow sensor, and a current environmental reading;
   means for comparing the measured airflow to a target value to obtain a result; and
   means for adjusting the operating speed of the air moving arrangement based on the result to maintain the measured airflow substantially in accordance with the target value.

38. The apparatus of claim 37 further comprising means for displaying the measured airflow.

39. The apparatus of claim 37 further comprising means for changing the target value in response to user input.

40. The apparatus of claim 37 further comprising means for sensing an external temperature for use by the means for calculating.

41. The apparatus of claim 40 further comprising:
   means for operating the air sampler for a plurality of sampling periods; and
   means for updating the measured airflow during one of the plurality of sampling periods based on a change in external temperature as indicated by the means for sensing the external temperature.

* * * * *

UNITED STATES PATENT AND TRADEMARK OFFICE
CERTIFICATE OF CORRECTION

| | |
|---|---|
| PATENT NO. | : 7,347,112 B2 |
| APPLICATION NO. | : 10/711585 |
| DATED | : March 25, 2008 |
| INVENTOR(S) | : Charles Gary Kay |

Page 1 of 1

It is certified that error appears in the above-identified patent and that said Letters Patent is hereby corrected as shown below:

Title page, item (73) Assignee should read as follows:
Environmental Monitoring Systems,
Inc., Charleston, SC (US)

Signed and Sealed this

Twenty-third Day of September, 2008

JON W. DUDAS
*Director of the United States Patent and Trademark Office*